US00PP08322P

United States Patent [19]

Vletter

[11] Patent Number: Plant 8,322

[45] Date of Patent: Jul. 27, 1993

[54] LILY PLANT NAMED MARCO POLO

[75] Inventor: Floris Vletter, Rijnsburg, Netherlands

[73] Assignee: Gebr. Vletter & J.A., Rijnsburg, Netherlands

[21] Appl. No.: 795,953

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new and distinct cultivar of lily plant named Marco Polo, characterized by its large, generally upright flowers, the base color of which is white infused with light pink, with pink being more prevalent near the distal end and along the midvein, vigorous growth habit, tall plant height, and its contrasting reddish brown pollen.

1 Drawing Sheet

The present invention comprises a new and distinct cultivar of lily, botanically known as Lilium, commercially known as Lilium oriental hybrid, and hereinafter referred to by the cultivar name Marco Polo. The parents were oriental varieties belonging to division VII(b) described in "Classification of Lily Cultivars into Divisions" published by Victoria Mathews, The Royal Botanic Gardens, Kew (1989).

The new cultivar is a product of a planned breeding program which had the objectives of creating new lily cultivars with a new soft pink color, larger semi-upright flowers, and having other desirable traits for use in cut flower production.

The new cultivar was originated from a hybridization made by the inventor in a controlled breeding program in Rijnsburg, The Netherlands in 1983. Both the male and the female parent were unnamed seedlings.

The new cultivar was discovered and selected as one flowering plant within the progeny of the stated cross by the inventor in July 1983 in a controlled environment in Rijnsburg, The Netherlands.

The first act of asexual reproduction of the new cultivar was accomplished by the inventor when scales were taken from the initial selection in 1987 in a controlled environment in Rijnsburg, The Netherlands.

Horticultural examination of selected units has demonstrated that the combination of characteristics as herein disclosed for Marco Polo are firmly fixed and are retained through successive generations of asexual reproduction.

The new cultivar has not been observed under all possible environmental conditions. The phenotype may vary somewhat with variations in environment such as temperature, light intensity, and day length, without, however, any variation in genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. Distinctive overall very light pink flower color, with pink becoming stronger near the distal end and along the midvein of the tepal;

2. Large, generally upright flowers;

3. Reddish brown pollen contrasts well with light pink flower color;

4. Vigorous, tall plant height.

Of the many commercial cultivars known to the present inventor, the most similar in comparison to the new cultivar is Stargazer. In comparison to Stargazer, Marco Polo has lighter pink flower color, longer stems, semi-erect flowers, and the fragrance of Marco Polo is milder. When flowering is forced under natural light, Marco Polo produces an inflorescence approximately 12 days earlier than stargazer, under the same growing conditions. Marco Polo is fertile.

The accompanying photographic drawing shows typical flower characteristics of the new cultivar, with colors being as true as possible with illustrations of this type. The photograph illustrates several open flowers and buds at various stages.

In the following description, color references are made to The Royal Horticultural Society (R.H.S.) Colour Chart. The color values were determined at Wageningen in 1989–1990 and at Rijnsburg in July 1991.

Origin: Seedling from Breeding Program.

Parentage:

*Seed parent.*—Unnamed seedling.

*Pollen parent.*—Unnamed seedling.

Classification:

*Botanical.*—Lilium.

*Commercial.*—Oriental hybrid.

The plant:

*Form.*—A single stem carrying numerous pedicels alternately arranged.

*Height.*—Medium to tall; 135 cm at time of opening of anthers of first flower.

*Growth habit.*—vigorous.

*Stem.*—Color 145A; circular in transverse section; internodal length uniform; anthocyanin pigmentation present.

*Foliage.*—Quantity: 45–55 leaves depending on growing conditions. Size of leaf: Mature leaves are medium in length (16 cm), and medium to broad in width (3.5 cm). Shape of leaves: Generally ovate. Texture: Smooth with weak glossiness on upper side; no pubescence lower side. Color: Medium green 137A.

*Bulbs.*—Size: Outlet 6–30 cm. Color: White and purple.

*Roots.*—Both stem and contractile present.

The bud:

*Form.*—Tapering.

*Size.*—10 cm prior to opening.

*Opening.*—Unfolds normally.

*Color.*—69B (color just prior to opening).

*Tepals.*—Folded, three visible.

The Flower:

*Blooming habit.*—Raceme.

*Size.*—Very large; 20 cm in total diameter, depending on growing conditions.

*Borne.*—Mostly upright, although the positioning or attitude of some flowers tends toward horizontal.

*Shape.*—Generally in form of hexagonal star, bowl-shaped in cross-section.

*Tepalage.*—Number of tepals: Six. Arrangement: Three inner and three outer each with marginal undulation. Color: Upper surface: Base color is white 155B with infusion of pink in varying amounts; distal ends and midveins are 65C to 62D. Lower surface: 155B to 62D. Spotting or marking: A few dark pink spots of 0.5–1.0 mm diameter appear on flowers.

*Nectaries and papillae.*—Present.

*Pedicel.*—Length: 10 cm. Color: Medium green. Form: Strongly curved.

*Texture.*—Papillose.

*Disease resistance.*—No disease problems noted to date.

*Fragrance.*—Present; medium strong.

*Lasting quality.*—Excellent.

Reproductive organs:

*Stamens, anthers.*—Arrangement: Anthers form a generally circular pattern. Length: Short to medium (7.5 cm). Number: Six. Filaments: Green.

*Pollen color.*—Reddish brown.

*Anther color.*—Yellowish brown.

*Pistils.*—Green, total length of pistil is 8.5 cm.

*Stigma.*—Purple.

*Ovaries.*—Triangular in shape other characteristics typical of oriental lily varieties.

I claim:

1. A new and distinct cultivar of lily plant named Marco Polo, as illustrated and described.

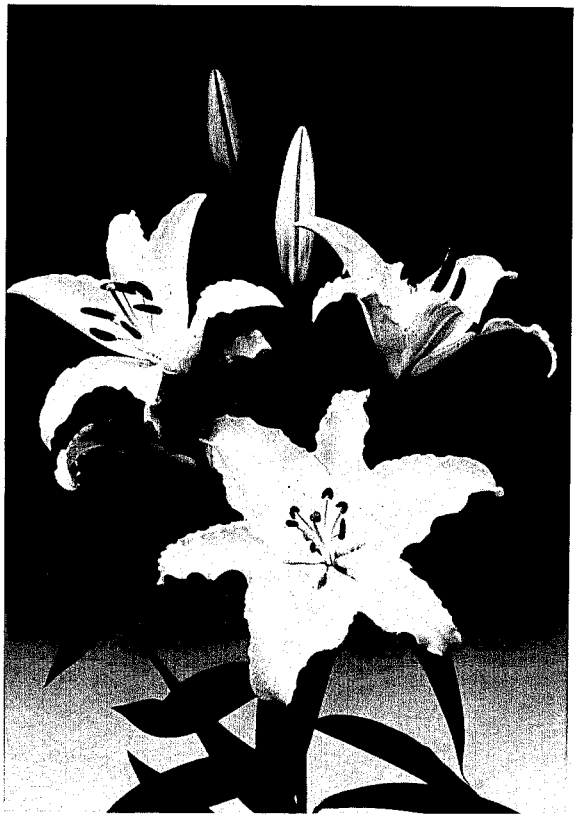

* * * * *